US008007772B2

(12) United States Patent
Dumousseaux et al.

(10) Patent No.: US 8,007,772 B2
(45) Date of Patent: Aug. 30, 2011

(54) COMPOSITIONS TO BE APPLIED TO THE SKIN AND THE INTEGUMENTS

(75) Inventors: Christophe Dumousseaux, Kawasaki (JP); Xavier Blin, Paris (FR); Ludovic Thevenet, Bourg la Reine (FR)

(73) Assignee: L'Oreal S.A., Paris (FR)

( * ) Notice: Subject to any disclaimer, the term of this patent is extended or adjusted under 35 U.S.C. 154(b) by 839 days.

(21) Appl. No.: 11/101,400

(22) Filed: Apr. 8, 2005

(65) Prior Publication Data

US 2006/0041054 A1 Feb. 23, 2006

Related U.S. Application Data

(63) Continuation-in-part of application No. 10/529,872, filed as application No. PCT/IB03/04306 on Oct. 1, 2003, now abandoned.

(60) Provisional application No. 60/428,723, filed on Nov. 25, 2002.

(30) Foreign Application Priority Data

Oct. 2, 2002 (FR) ..................... 02 12215
Apr. 8, 2004 (FR) ..................... 04 50712
Apr. 8, 2004 (FR) ..................... 04 50713
Apr. 8, 2004 (FR) ..................... 04 50714
Apr. 8, 2004 (FR) ..................... 04 50715

(51) Int. Cl.
*A61K 8/00* (2006.01)
(52) U.S. Cl. .......................... 424/63; 424/60
(58) Field of Classification Search ............... 424/401
See application file for complete search history.

(56) References Cited

U.S. PATENT DOCUMENTS

| | | | |
|---|---|---|---|
| 3,030,967 A | 4/1962 | Peyron | |
| 3,516,422 A | 6/1970 | Bechtold et al. | |
| 3,836,537 A | 9/1974 | Boerwinkle et al. | |
| 3,910,862 A | 10/1975 | Barabas et al. | |
| 3,926,659 A | 12/1975 | Bernhard et al. | |
| 3,937,811 A | 2/1976 | Papantoniou et al. | |
| 4,031,307 A | 6/1977 | DeMartino et al. | |
| 4,055,377 A | 10/1977 | Erickson et al. | |
| 4,131,576 A | 12/1978 | Iovine et al. | |
| 4,223,009 A | 9/1980 | Chakrabarti | |
| 4,318,844 A | 3/1982 | Kohler et al. | |
| 4,693,935 A | 9/1987 | Mazurek | |
| 4,728,571 A | 3/1988 | Clemens et al. | |
| 4,972,037 A | 11/1990 | Garbe et al. | |
| 4,981,902 A | 1/1991 | Mitra et al. | |
| 4,981,903 A | 1/1991 | Garbe et al. | |
| 5,030,669 A * | 7/1991 | Hendrickson et al. | ......... 523/333 |
| 5,040,914 A | 8/1991 | Fitjer | |
| 5,061,481 A | 10/1991 | Suzuki et al. | |
| 5,066,485 A * | 11/1991 | Brieva et al. | ............ 424/63 |
| 5,122,418 A * | 6/1992 | Nakane et al. | ............ 424/401 |
| 5,133,805 A | 7/1992 | Kurata et al. | |
| 5,162,410 A | 11/1992 | Sweet | |
| 5,188,899 A | 2/1993 | Matsumoto et al. | |
| 5,199,808 A | 4/1993 | Gueret | |
| 5,209,924 A | 5/1993 | Garbe et al. | |
| 5,219,560 A | 6/1993 | Suzuki et al. | |
| 5,316,026 A | 5/1994 | Jenkins | |
| 5,330,747 A | 7/1994 | Krzysik | |
| 5,356,617 A * | 10/1994 | Schlossman | ................ 424/401 |
| 5,362,485 A | 11/1994 | Hayama et al. | |
| 5,380,359 A | 1/1995 | Honda et al. | |
| 5,424,006 A | 6/1995 | Murayama et al. | |
| 5,451,610 A | 9/1995 | Krzysik | |
| 5,468,477 A | 11/1995 | Kumar et al. | |
| 5,472,798 A | 12/1995 | Kumazawa et al. | |
| 5,486,354 A | 1/1996 | Defossez et al. | |
| 5,512,273 A | 4/1996 | Martin | |
| 5,562,706 A | 10/1996 | Lauterbach et al. | |
| 5,625,005 A | 4/1997 | Mallya et al. | |
| 5,641,835 A | 6/1997 | Smith et al. | |
| 5,643,672 A | 7/1997 | Marchi et al. | |
| 5,658,574 A | 8/1997 | Bahary et al. | |
| 5,683,706 A | 11/1997 | LaFleur et al. | |
| 5,725,882 A | 3/1998 | Kumar et al. | |
| 5,846,310 A | 12/1998 | Noguchi et al. | |
| 5,849,275 A | 12/1998 | Calello et al. | |
| 5,849,318 A | 12/1998 | Imai et al. | |
| 5,851,517 A | 12/1998 | Mougin et al. | |
| 5,856,653 A | 1/1999 | Boudreaux | |

(Continued)

FOREIGN PATENT DOCUMENTS

DE        102 19 196        11/2003

(Continued)

OTHER PUBLICATIONS

"Precise Color Communication." Konica Miniolta Sensing, Inc. 1998.*
Precise Color Communciations, Konica Minolta Sensing, Inc 1998.*
Minolta, Precise Color Communication, Color Control From Perception to Instrumentation.*
Precise Color Communications, Konica Minolta Sensing, Inc 1998.*
English language Abstract of JP 4-292664, Oct. 16, 1992.
English language Abstract of JP 11-181329, Jul. 6, 1999.
English language Abstract of JP 2003-000338, Jan. 7, 2003.
English language Abstract of JP 2004-043367, Feb. 12, 2004.
English language Abstract of JP 2004-123681, Apr. 22, 2004.

(Continued)

*Primary Examiner* — Anand Desai
*Assistant Examiner* — Melissa Mercier
(74) *Attorney, Agent, or Firm* — Finnegan, Henderson, Farabow, Garrett & Dunner LLP

(57) ABSTRACT

The present disclosure relates a cosmetic composition comprising in a physiologically acceptable medium at least one composite pigment comprising an inorganic core at least partially coated with at least one organic coloring substance, wherein the color variation ΔE between the color of the bulk composition and the color after application is less than about 20.

43 Claims, No Drawings

U.S. PATENT DOCUMENTS

| | | | |
|---|---|---|---|
| 5,873,375 A | 2/1999 | Johnson et al. | |
| 5,874,069 A | 2/1999 | Mendolia et al. | |
| 5,919,441 A | 7/1999 | Mendolia et al. | |
| 5,931,166 A | 8/1999 | Weber et al. | |
| 5,948,393 A | 9/1999 | Tomomasa et al. | |
| 5,954,871 A | 9/1999 | Nicolas-Morgantini et al. | |
| 5,981,680 A | 11/1999 | Petroff et al. | |
| 6,001,338 A | 12/1999 | Mondet | |
| 6,033,650 A | 3/2000 | Calello et al. | |
| 6,051,216 A | 4/2000 | Barr et al. | |
| 6,071,632 A | 6/2000 | Hall-Goulle | |
| 6,074,654 A | 6/2000 | Dreschler et al. | |
| 6,117,435 A | 9/2000 | Painter et al. | |
| 6,117,574 A | 9/2000 | Watanabe et al. | |
| 6,177,093 B1* | 1/2001 | Lombardi et al. | 424/401 |
| 6,203,781 B1 | 3/2001 | Chevalier et al. | |
| 6,209,548 B1 | 4/2001 | Harrison et al. | |
| 6,280,655 B1 | 8/2001 | Xu et al. | |
| 6,299,979 B1 | 10/2001 | Neubauer et al. | |
| 6,358,495 B1 | 3/2002 | Nishihama et al. | |
| 6,387,498 B1 | 5/2002 | Coulter et al. | |
| 6,403,106 B1 | 6/2002 | Sebag et al. | |
| 6,428,773 B1 | 8/2002 | Oko et al. | |
| 6,432,386 B1 | 8/2002 | Rollat-Corvol et al. | |
| 6,432,423 B1 | 8/2002 | Maignan et al. | |
| 6,491,927 B1 | 12/2002 | Arnaud et al. | |
| 6,503,761 B1 | 1/2003 | Koenig et al. | |
| 6,517,818 B1 | 2/2003 | Golz-Berner et al. | |
| 6,545,809 B1 | 4/2003 | Phillips | |
| 6,589,331 B2 | 7/2003 | Ostertag et al. | |
| 6,669,389 B2 | 12/2003 | Gueret | |
| 6,753,002 B2 | 6/2004 | George et al. | |
| 6,846,474 B2 | 1/2005 | Nayfeh et al. | |
| 7,056,498 B2 | 6/2006 | Chevalier et al. | |
| 7,060,371 B2 | 6/2006 | Akiyama et al. | |
| 7,168,874 B2 | 1/2007 | Gueret | |
| 7,258,900 B2 | 8/2007 | Raksha et al. | |
| 7,270,770 B2 | 9/2007 | Sage et al. | |
| 7,329,287 B2 | 2/2008 | Simonet et al. | |
| 7,329,719 B2 | 2/2008 | Pavlin | |
| 2001/0022025 A1 | 9/2001 | Skipper | |
| 2001/0033766 A1 | 10/2001 | Gueret | |
| 2002/0012683 A1* | 1/2002 | Henrion et al. | 424/401 |
| 2002/0015965 A1 | 2/2002 | Sweeting | |
| 2002/0031870 A1 | 3/2002 | Bryant | |
| 2002/0039562 A1 | 4/2002 | Kobayashi et al. | |
| 2002/0041853 A1 | 4/2002 | Ishii et al. | |
| 2002/0064509 A1 | 5/2002 | Grimm et al. | |
| 2002/0070121 A1 | 6/2002 | Nayfeh et al. | |
| 2002/0117084 A1 | 8/2002 | Hayashi et al. | |
| 2002/0134282 A1 | 9/2002 | Ostertag et al. | |
| 2002/0169244 A1 | 11/2002 | Ostertag et al. | |
| 2002/0182383 A1 | 12/2002 | Phillips et al. | |
| 2002/0182409 A1 | 12/2002 | Gueret | |
| 2003/0007942 A1 | 1/2003 | Koenig | |
| 2003/0012752 A1 | 1/2003 | Bara | |
| 2003/0017124 A1 | 1/2003 | Agostini et al. | |
| 2003/0031870 A1 | 2/2003 | Argoitia et al. | |
| 2003/0039621 A1 | 2/2003 | Arnaud et al. | |
| 2003/0064039 A1 | 4/2003 | Kolodziej et al. | |
| 2003/0072602 A1 | 4/2003 | Gueret | |
| 2003/0134761 A1 | 7/2003 | Sebillotte-Arnaud et al. | |
| 2003/0180232 A1 | 9/2003 | Ishii et al. | |
| 2003/0180535 A1 | 9/2003 | Horino et al. | |
| 2004/0001869 A1 | 1/2004 | Yago et al. | |
| 2004/0009309 A1 | 1/2004 | Raksha et al. | |
| 2004/0012683 A1* | 1/2004 | Yamasaki et al. | 348/208.1 |
| 2004/0105827 A1 | 6/2004 | Grimm et al. | |
| 2004/0109837 A1 | 6/2004 | Mellul et al. | |
| 2004/0175338 A1 | 9/2004 | Filippi et al. | |
| 2004/0228818 A1 | 11/2004 | Simon et al. | |
| 2004/0228890 A1 | 11/2004 | Blin et al. | |
| 2004/0241118 A1 | 12/2004 | Simon et al. | |
| 2005/0025728 A1 | 2/2005 | De Rigal et al. | |
| 2005/0036964 A1 | 2/2005 | Camus et al. | |
| 2005/0118122 A1 | 6/2005 | Simon et al. | |
| 2005/0191337 A1 | 9/2005 | Gueret | |
| 2005/0276767 A1 | 12/2005 | Blin et al. | |
| 2006/0018854 A1 | 1/2006 | Dumousseaux et al. | |
| 2006/0039876 A1 | 2/2006 | Dumousseaux et al. | |
| 2006/0041054 A1 | 2/2006 | Dumousseaux et al. | |
| 2006/0051382 A1 | 3/2006 | Vidal | |
| 2006/0088484 A1 | 4/2006 | Thevenet | |
| 2006/0099160 A1 | 5/2006 | Dumousseaux | |
| 2006/0165621 A1 | 7/2006 | Dubertret et al. | |
| 2006/0282764 A1 | 12/2006 | Lee et al. | |
| 2007/0009454 A1 | 1/2007 | Thevenet | |
| 2007/0231940 A1 | 10/2007 | Gourlaouen et al. | |
| 2008/0014158 A1 | 1/2008 | Lion et al. | |
| 2008/0044443 A1 | 2/2008 | Thevenet | |
| 2008/0050324 A1 | 2/2008 | Thevenet | |
| 2008/0105272 A1 | 5/2008 | Thevenet | |
| 2008/0124288 A1 | 5/2008 | Thevenet | |
| 2008/0127990 A1 | 6/2008 | Thevenet | |
| 2009/0130037 A1 | 5/2009 | Thevenet et al. | |

FOREIGN PATENT DOCUMENTS

| | | |
|---|---|---|
| DE | 102 19 296 | 11/2003 |
| EP | 0 080 976 | 6/1983 |
| EP | 0 096 459 | 12/1983 |
| EP | 0 113 920 | 7/1984 |
| EP | 0 388 582 | 9/1990 |
| EP | 0 412 704 | 2/1991 |
| EP | 0 412 707 | 2/1991 |
| EP | 0 416 747 | 3/1991 |
| EP | 0 581 651 | 2/1994 |
| EP | 0 582 152 | 2/1994 |
| EP | 0 587 908 | 3/1994 |
| EP | 0 686 858 | 12/1995 |
| EP | 0 749 747 | 12/1996 |
| EP | 0 815 836 | 1/1998 |
| EP | 0921217 | 12/1998 |
| EP | 0 955 039 | 10/1999 |
| EP | 0 962 224 | 12/1999 |
| EP | 1 043 018 | 10/2000 |
| EP | 1 101 486 | 5/2001 |
| EP | 1 184 426 | 3/2002 |
| EP | 1 217 046 | 6/2002 |
| EP | 1 264 562 | 12/2002 |
| EP | 1 318 184 | 6/2003 |
| EP | 1 382 323 | 1/2004 |
| EP | 1 410 786 | 4/2004 |
| EP | 1 411 069 | 4/2004 |
| EP | 1 424 372 | 6/2004 |
| EP | 1 440 681 | 7/2004 |
| FR | 2 077 143 | 10/1971 |
| FR | 2 232 303 | 1/1975 |
| FR | 2 268 512 | 11/1975 |
| FR | 2 393 573 | 1/1979 |
| FR | 2 594 130 | 8/1987 |
| FR | 2 845 277 | 4/2004 |
| FR | 2 845 899 | 4/2004 |
| FR | 2 847 812 | 6/2004 |
| FR | 2 848 821 | 6/2004 |
| FR | 2 848 826 | 6/2004 |
| FR | 2 850 271 | 7/2004 |
| FR | 2 851 463 | 8/2004 |
| GB | 1 331 819 | 9/1973 |
| GB | 1 510 674 | 5/1978 |
| GB | 2 355 987 | 5/2001 |
| JP | 51-137733 | 11/1976 |
| JP | 55-081809 | 6/1980 |
| JP | 58-206610 | 12/1983 |
| JP | 61-112008 | 5/1986 |
| JP | 63-175670 | 7/1988 |
| JP | 1-294611 | 11/1989 |
| JP | 2-111340 | 4/1990 |
| JP | 04-108710 | 8/1990 |
| JP | 3-284613 | 12/1991 |
| JP | 3-286463 | 12/1991 |
| JP | 4-292664 | 10/1992 |
| JP | 5-17710 | 1/1993 |
| JP | 7-258460 | 10/1995 |
| JP | 3-286463 | 11/1995 |
| JP | 7-304633 | 11/1995 |
| JP | 7-304997 | 11/1995 |
| JP | 7-316015 | 12/1995 |

| | | |
|---|---|---|
| JP | 8-127513 | 5/1996 |
| JP | 9-188830 | 7/1997 |
| JP | 10-158450 | 6/1998 |
| JP | 10-158541 | 6/1998 |
| JP | 2000-143490 | 11/1998 |
| JP | 11-012493 | 1/1999 |
| JP | 11-113631 | 4/1999 |
| JP | 11-181329 | 7/1999 |
| JP | 2001-61550 | 3/2001 |
| JP | 2001-299443 | 10/2001 |
| JP | 2002-188021 | 7/2002 |
| JP | 2002-194349 | 7/2002 |
| JP | 2002-322020 | 11/2002 |
| JP | 2003-000338 | 1/2003 |
| JP | 2003-024133 | 1/2003 |
| JP | 2003-199620 | 7/2003 |
| JP | 2004-043367 | 2/2004 |
| JP | 2004-043656 | 2/2004 |
| JP | 2004-059746 | 2/2004 |
| JP | 2004-123681 | 4/2004 |
| JP | 2004-131484 | 4/2004 |
| JP | 2004-307424 | 11/2004 |
| JP | 2005-232152 | 9/2005 |
| WO | WO 93/23009 | 11/1993 |
| WO | WO 93/23446 | 11/1993 |
| WO | WO 94/26729 | 11/1994 |
| WO | WO 95/00578 | 1/1995 |
| WO | WO 95/03776 | 2/1995 |
| WO | WO 95/06078 | 3/1995 |
| WO | WO 96/19347 | 6/1996 |
| WO | WO 97/35541 | 10/1997 |
| WO | WO 99/32076 | 7/1999 |
| WO | WO 99/36477 | 7/1999 |
| WO | WO 99/36478 | 7/1999 |
| WO | WO 01/38222 | 5/2001 |
| WO | WO 02/28356 | 4/2002 |
| WO | WO 03/016429 | 2/2003 |
| WO | WO 03/020225 | 3/2003 |
| WO | WO 2004/000244 | 12/2003 |
| WO | WO 2004/007096 | 1/2004 |
| WO | WO 2004/009044 | 1/2004 |
| WO | WO 2006/027494 | 3/2006 |
| WO | WO 2006/037900 | 4/2006 |
| WO | WO 2006/037902 | 4/2006 |

OTHER PUBLICATIONS

English language Abstract of JP 2004-307424, Nov. 4, 2004.
English language Abstract of JP 61-112008, May 30, 1986.
English language Abstract of JP 7-316015, Dec. 5, 1995.
Argoitia, A. et al., "Pigments Exhibiting Diffractive Effects", Society of Vacuum Coaters, 45th Annual Technical Conference Proceedings, pp. 539-545, (2002).
Co-pending U.S. Appl. No. 10/529,872, filed Apr. 1, 2005.
Co-pending U.S. Appl. No. 11/100,509, filed Apr. 7, 2005.
Co-pending U.S. Appl. No. 11/100,513, filed Apr. 7, 2005.
Co-pending U.S. Appl. No. 11/100,514, filed Apr. 7, 2005.
Co-pending U.S. Appl. No. 11/100,566, filed Apr. 7, 2005.
Co-pending U.S. Appl. No. 11/101,398, filed Apr. 8, 2005.
Co-pending U.S. Appl. No. 11/101,399, filed Apr. 8, 2005.
Co-pending U.S. Appl. No. 11/242,900, filed Oct. 5, 2005.
Co-pending U.S. Appl. No. 11/242,901, filed Oct. 5, 2005.
English language Abstract of DE 102 19 296, Nov. 20, 2003.
English language Patent Abstract of Japan of JP 04-108710, Aug. 27, 1990.
English language Patent Abstract of Japan of JP 10-158541, Jun. 16, 1998.
English language Patent Abstract of Japan of JP 10-158450, Jun. 16, 1998.
English language Patent Abstract of Japan of JP 11 012493, Jan. 19, 1999.
English language Patent Abstract of Japan of JP 1-294611, Nov. 28, 1989.
English language Patent Abstract of Japan of JP 2000-143490, Nov. 9, 1998.
English language Patent Abstract of Japan of JP 2003-199620, Jul. 15, 2003.
English language Patent Abstract of Japan of JP 2-111340, Apr. 24, 1990.
English language Patent Abstract of Japan of JP 3-286463, Dec. 17, 1991.
English language Patent Abstract of Japan of JP 5-17710, Jan. 26, 1993.
English language Patent Abstract of Japan of JP 7-258460, Oct. 9, 1995.
English language Patent Abstract of Japan of JP 7-304633, Nov. 21, 1995.
English language Patent Abstract of Japan of JP 7-304997, Nov. 21, 1995.
English language Patent Abstract of Japan of JP 8-127513, May 21, 1996.
English language Patent Abstract of Japan of JP 9-188830, Jul. 22, 1997.
French Search Report for French Patent Application No. FR 04/50712, priority document for co-pending U.S. Appl. No. 11/100,513, Nov. 9, 2004.
French Search Report for French Patent Application No. FR 04/50713, priority document for co-pending U.S. Appl. No. 11/100,566, Nov. 23, 2004.
French Search Report for French Patent Application No. FR 04/50714, priority document for co-pending U.S. Appl. No. 11/100,509, Nov. 10, 2004.
French Search Report for French Patent Application No. FR 04/50715, priority document for co-pending U.S. Appl. No. 11/100,514, Nov. 23, 2004.
French Search Report for French Patent Application No. FR 05/52124, May 24, 2006.
Furst, E. et al., "Permanently Linked Monodisperse Paramagnetic Chains", Langmuir, vol. 14, pp. 7334-7336 (1998).
Goubault, C., "Flexible Magnetic Filaments as Micromechanical Sensors", Physical Review Letters, vol. 91, No. 26, pp. 1-4 (2003).
International Cosmetic Ingredient Dictionary and Handbook, 1997 Edition, pp. 371-386.
International Cosmetic Ingredient Dictionary and Handbook, 1997 Edition, pp. 524-528.
International Search Report for PCT Application No. PCT/IB03/04306, priority document for co-pending U.S. Appl. No. 10/529,872, dated Mar. 3, 2004.
International Search Report for PCT/FR2005/050557, priority document for co-pending U.S. Appl. No. 11/242,901, Feb. 10, 2006.
Office Action mailed Dec. 28, 2006 in co-pending U.S. Appl. No. 11/100,509.
"Graft Copolymers with Short Side Chains," Polymer Letters, 1967, vol. 5, pp. 477-481.
Fermigier, et al., "Suspensions de Particules Magnetiques," Bulletin de la S.F.P. (105): pp. 2-5, Jul. 1996.
Goubault, "Colloides Magnetiques: Auto-Organisation et Applications Biologiques," Doctoral Thesis of the University of Paris VI, Mar. 23, 2004.
Hansen, C.M., "The Three Dimensional Solubility Parameter—Key to Paint Component Affinities: I. Solvents, Plasticizers, Polymers, and Resins," Journal of Paint Technology, vol. 39, No. 505, pp. 104-117 (1967).
Office Action mailed Jan. 21, 2010, in co-pending U.S. Appl. No. 11/242,901.
Office Action mailed Jul. 7, 2009, in copending U.S. Appl. No. 11/242,901.
Office Action mailed Nov. 9, 2009, in co-pending U.S. Appl. No. 11/101,400.
Office Action mailed Oct. 1, 2009, in co-pending U.S. Appl. No. 11/101,398.
Office Action mailed Oct. 26, 2009, in co-pending U.S. Appl. No. 11/100,513.
Office Action mailed Sep. 24, 2009, in co-pending U.S. Appl. No. 11/101,399.
Office Action mailed Apr. 27, 2010, in co-pending U.S. Appl. No. 11/770,177.
Office Action mailed Apr. 28, 2010, in co-pending U.S. Appl. No. 11/100,566.

Office Action mailed Aug. 3, 2010, in co-pending U.S. Appl. No. 11/101,399.
Office Action mailed Aug. 4, 2010, in co-pending U.S. Appl. No. 11/101,398.
Office Action mailed Jul. 7, 2010, in co-pending U.S. Appl. No. 11/242,901.
Office Action mailed May 11, 2010, in co-pending U.S. Appl. No. 11/100,513.
Drahl, "Nail Polish", 2008, American Chemical Society, Chemical & Engineering News, vol. 86, No. 32, p. 32.
English language Abstract of JP 51-137733, dated Nov. 27, 1976.
English language Abstract of JP 63-175670, dated Jul. 20, 1988.
Japanese Office Action in related Application No. 2007-534054, dated Oct. 7, 2010.
Office Action mailed Dec. 21, 2010, in co-pending U.S. Appl. No. 11/100,513.
Office Action mailed Dec. 22, 2010, in co-pending U.S. Appl. No. 11/242,901.
Office Action mailed Dec. 23, 2010, in co-pending U.S. Appl. No. 11/242,900.
Co-pending U.S. Appl. No. 11/770,177, filed Jun. 28, 2007.
Japanese Publication S55-81809, Kiyoshi Inoue, Method of Magnatized Cosmetic Agent Usage, Jun. 20, 1980.
Office Action mailed Jan. 15, 2009, in co-pending U.S. Appl. No. 11/100,514.
Office Action mailed Jan. 27, 2009, in co-pending U.S. Appl. No. 11/770,177.
Office Action mailed Jan. 7, 2009, in co-pending U.S. Appl. No. 11/100,566.
Office Action mailed Jan. 8, 2009, in co-pending U.S. Appl. No. 11/242,901.
Office Action mailed Jul. 10, 2009, in co-pending U.S. Appl. No. 11/770,177.
Office Action mailed Jul. 9, 2009, in co-pending U.S. Appl. No. 11/100,566.
Office Action mailed Jun. 23, 2008, in co-pending U.S. Appl. No. 11/101,399.
Office Action mailed Jun. 23, 2008, in co-pending U.S. Appl. No. 11/242,901.
Office Action mailed Jun. 24, 2008, in co-pending U.S. Appl. No. 11/100,566.
Office Action mailed Jun. 24, 2008, in co-pending U.S. Appl. No. 11/770,177.
Office Action mailed Jun. 26, 2008, in co-pending U.S. Appl. No. 11/101,398.
Office Action mailed Mar. 19, 2009, in co-pending U.S. Appl. No. 11/101,398.
Office Action mailed Mar. 19, 2009, in co-pending U.S. Appl. No. 11/101,399.
Office Action mailed May 21, 2009, in co-pending U.S. Appl. No. 11/100,513.
Patent Abstract of Japan for JP 11-113631, Apr. 27, 1999.
Patent Abstract of Japan for JP 2001-61550, Mar. 13, 2001.
Titanium Dioxide—Wikipedia (http://en.wikipedia.org/wiki/Titanium_dioxide.retrieved online on Jun. 19, 2008).

* cited by examiner

COMPOSITIONS TO BE APPLIED TO THE SKIN AND THE INTEGUMENTS

This application is a continuation-in-part of non-provisional U.S. patent application Ser. No. 10/529,872, filed Oct. 12, 2005, now abandoned which is a national phase entry of International Application No. PCT/IB2003/004306, filed Oct. 1, 2003, which claims priority to French Application No. FR 02 12215, filed Oct. 2, 2002, and provisional U.S. Patent Application No. 60/428,723, filed Nov. 25, 2002, all of which are hereby incorporated by reference. This application also claims priority to French Patent Application No. FR 04 50712, filed Apr. 8, 2004, French Patent Application No. FR 04 50713, filed Apr. 8, 2004, French Patent Application No. FR 04 50714, filed Apr. 8, 2004, and French Patent Application No. FR 04 50715, filed Apr. 8, 2004, all of which are hereby incorporated by reference.

Other compositions and methods are disclosed in co-pending U.S. patent application Ser. No. 11/100,509, filed Apr. 7, 2005, U.S. patent application Ser. No. 11/100,566, filed Apr. 7, 2005, U.S. patent application Ser. No. 11/100,514, filed Apr. 7, 2005, and U.S. patent application Ser. No. 11/100,513, filed Apr. 7, 2005, all of which are hereby incorporated by reference.

The present disclosure relates to compositions intended to be applied to the skin, including mucous membranes such as the lips, and the integuments, such as the nails, the eyelashes, the eyebrows and the hair.

It is known practice to incorporate organic coloring substances into cosmetic compositions, these pigments making it possible to obtain colors with high saturation. However, their covering power is poor, which leads to mineral pigments being added to the composition.

The presence in the composition of a mixture of pigments of different nature entails a risk of variability of the properties, especially when different shades are produced by changing the proportions of organic and mineral pigments. This is because the behavior of the organic and mineral pigments towards the other constituents of the composition may not be the same, which results in difficulties of formulation. Thus, the sticks of a range of shades of lipsticks will have variable hardnesses.

Furthermore, the behavior of the organic and mineral pigments towards the other constituents of the composition may be different, which results in difficulties of formulation and a risk of modification of the makeup result over time, for example when a volatile compound evaporates. Thus, for example, certain lipsticks comprise mineral pigments such as $TiO_2$ and an oily phase; the $TiO_2$ particles may become white when they are no longer coated with the oily phase, which changes the color of the composition applied and poses a problem of stability of the color over time.

When lakes are used, the organic dye used in the lake may transfer onto the support and stain it. The pigments conventionally used in cosmetic formulations are about one micrometer or larger in size. This large size, combined with a high density, may result in sedimentation and stability problems in liquid formulations. It may also prevents the production of transparency effects associated with a large saturation of the color.

There is also a need for a composition which exhibits a color after application that is as little different as possible from the color of the bulk composition. Thus the user can obtain after application a color result that is close to what was expected in view of the composition before application.

The present disclosure relates to a cosmetic composition comprising, in a physiologically acceptable medium, at least one composite pigment comprising an inorganic core at least partially coated with at least one organic coloring substance.

The color variation ΔE between the color of the bulk composition and the color after application may be less than about 20, such as less than about 15, for example less than 10.

Protocol for Measuring ΔE

Color Values $L^*_{bulk}$ $a^*_{bulk}$ and $b^*_{bulk}$ of the Bulk Composition:

The color is measured using a Murakami CMS-35FS spectrocolorimeter with an optical fiber, under illuminant D65, aperture 3 mm and an angle of 10°. The optical fiber is put into contact with the composition.

The L*a*b* values in the CIE L*a*b* color space are measured six times and averaged. The color parameter $L^*_{bulk}$ $a^*_{bulk}$ $b^*_{bulk}$ for the bulk composition results from the average values.

When the composition is a solid, for example a stick, the color can be measured directly on the stick. Otherwise, the measurement of $a^*_{bulk}$, $b^*_{bulk}$ and $L^*_{bulk}$ is made on a layer of product that is at least 3 mm thick.

When the product is a powder, the measurement can be made after the composition is compacted in a rectangular cup having a depth of 3 mm and dimensions of 2×1.5 cm, under a pressure of 100 bars.

Color Parameters $L^*_{application}$, $a^*_{application}$ and $b^*_{application}$ of the Composition After Application:

The composition is applied manually or otherwise to form a layer of 1 mg/cm² on a Bio Skin® substrate having L*=69, a*=11.5 and b*=19.7 color coordinates. The Bio Skin® substrate which is 5 mm thick and has smooth surface is commercialized by the Japanese company Beaulax under the reference Bioskin #10, format A4.

The $L^*_{application}$, $a^*_{application}$ and $b^*_{application}$ parameters are measured ten times and then averaged.

ΔE is given by $$[(a^*_{bulk} - a^*_{application})^2 + (b^*_{bulk} - b^*_{application})^2 + (L^*_{bulk} - L^*_{application})^2]^{\frac{1}{2}}.$$

The saturation $C^*_{bulk}$ of the composition may be greater than 25, 30 or 40.

The saturation $C^*_{application}$ of the composition after application may be greater than 30, for example greater than 40.

The saturation of the composition after application $C^*_{application}$ is defined by $(a^{*}_{application}{}^2 + b^{*}_{application}{}^2)^{1/2}$, where $a^*_{application}$ and $b^*_{application}$ are measured as explained above.

The saturation $C^*_{bulk}$ is defined by $(a^{*}_{bulk}{}^2 + b^{*}_{bulk}{}^2)^{1/2}$.

In one embodiment, the composition comprises at least one additional coloring agent, for example an organic lake or other pigment.

The quantity of the additional coloring agent may be less than that of the composite pigment.

The composite pigment may be present in an amount greater than 10%, for example greater than 12.5% or 15%, by weight relative to the total weight of the composition.

The additional coloring agent may be present in the composition in an amount not larger than 5% by weight relative to the total weight of the composition.

The mean gloss $T_0h$ of the composition, for example in some exemplary embodiments where the composition is liquid, may be greater than 30, or 35, or 40, or 45, or 50, or 55, or 60, or 65, or 70 or 75.

Protocol for Measuring the Mean Gloss $T_0h$:

On a contrast card of the brand BYK Gardner and of reference Prüfkarten, Art. 2853, previously fixed on a glass plate of 1 mm of thickness, a layer of 25 µm of thickness of the composition is sprayed using an automatic sprayer (Bar coater, Sheen).

The layer covers at least the black background of the card.

When the composition is a solid, the composition is melted if necessary on the card after having spread it so that it covers the black background.

As soon as the composition is spread, the mean gloss is measured, at 60°, on the black background of the card using a BYK GARDNER Brand glossmeter of reference micro TRI-GLOSS.

This procedure is reported for four contrast cards to measure the mean gloss of the composition and to compute the average of the four values, $T_0h$.

The measure is deemed to be correct when the standard deviation of the four values is less or equal to 3%.

The mean gloss $T_5h$ after five hours can also be measured.

The contrast card is left for five hours on a thermostated plate at a temperature of 30° C.

After five hours, the contrast card is withdrawn from the thermostated plate so that it comes back to room temperature and the mean gloss at 60° is measured again to determine the mean gloss $T_5h$, by averaging four values.

In some embodiments when gloss is sought, the mean gloss $T_0h$ of the composition may be greater than 45 or even greater than 50, or 60, or 65, or 70, or even 75.

The mean gloss $T_5h$ may be greater than or equal to 35, or 40, or 45, or 50, or 55, or 60, or 65 or 70, or even 75, out of 100.

The relative proportion Q of the particulate phase in the composition may be not less than 5%, such as not less than 7.5% or not less than 10% or more. In other embodiments, the particulate phase may be present in the composition in an amount not less than 15%, 20% or 30%.

The use of composite pigments in the present disclosure may enable one to achieve a relatively high gloss notwithstanding a relatively high amount of the particulate phase.

Protocol for Measuring the Proportion Q of the Particulate Phase:

A Soxhlet extractor comprising a cartridge, a fat flask, a flask heater and a condenser is used.

To begin the Soxhlet extractor cartridge is regenerated by boiling about 80 ml of toluene in the fat flask so that the cycles lasts about ½ h. The cartridge is allowed to cool and dry overnight in the oven and then in the dessicator.

A PTFE membrane having a known weight $T_1$ is folded in a cone and inserted into the cartridge. Precisely 0.75 g (m) of the composition is weighted in the membrane and the latter is folded in the cartridge so that it is well closed.

The cartridge is put in the Soxhlet extractor after having introduced a small perforated flask, serving to maintain the top of the cartridge a little above the elbow of the Soxhlet extractor to prevent the level of toluene to exceed the top end of the cartridge and to prevent the displacement of the composition.

80 ml of toluene are added in the fat flask.

The condenser is started and then heats the fat flask so that the toluene boils (boiling point 100.6° C.) with reflux for four hours.

The vapors of toluene have to condensate at the first ball of the condenser and the condensation must not be too fast. The condenser is allowed to cool and then switched off.

The cartridge is dried in the oven for two days and left in the dessicator for at least two hours, and the dry cartridge is weighed ($T_2$) immediately after leaving the dessicator.

The test is made on at least two samples.

The relative proportion of particulate phase, i.e. materials not soluble in hot toluene, is given by $Q=((T_2-T_1)/m) \times 100$.

The use of a composite pigment comprising an inorganic core at least partially covered by an organic coating may provide a glossy composition notwithstanding a relatively high amount of particulate phase.

The covering power of the composition may exceed in some embodiments 25, and in some other embodiments the covering power may be less than 25. For example, the covering power in some embodiments may range from 1 to 25. The covering power may be different from 25.

When the covering power exceeds 25, the covering power may be greater than 30, or 40, or 50, or 60, or 70, or 80, or 90, if a high covering power is sought.

The covering power may depend from the quantity of composite pigment and filler, if any.

Protocol for Measuring the Covering Power

For a stick, the formulation is initially ground down so as to obtain a viscous paste.

For a powder, 50 parts by weight of the power are ground down with 50 parts by weight of dimethicon (DOW CORNING DC 200 Fluid 5CST) so as to obtain a viscous paste.

Then, the formulation is spread to a thickness of 30 micrometers (µm) on an Erichsen contrast card, type 24/5, that presents a black background and a white background, and the (X, Y, Z) chromaticity coordinates are measured by means of a CR-300 colorimeter.

The composition is similarly spread on other contrast cards and three measurements are taken for each card. The average of these nine measurements is then calculated.

The covering power is equal to $100 \times Yn/Yb$, where Yn is the average value of Y on a black background and Yb is the average value of Y on a white background. A covering power of 100 corresponds to a formulation that is completely opaque.

The color parameter $\Delta_{a^*b^*pigment}$ of the at least one organic coloring substance of the composite pigment may be greater than about 5.

In some exemplary embodiments, $\Delta_{a^*b^*pigment}$ may be greater than about 10, or even 15 or 20 or more, such as, for example, 25.

Protocol for Measuring the Color Parameter $\Delta_{a^*b^*pigment}$

The color parameter $\Delta_{a^*b^*pigment}$ is defined by $$\Delta_{a^*b^*pigment} = \left[ \begin{matrix} (a^*_{raw\ organic\ pigment} - a^*_{composite\ pigment})^2 + \\ (b^*_{raw\ organic\ pigment} - b^*_{composite\ pigment})^2 \end{matrix} \right]^{\frac{1}{2}}$$

The color values a* and b* in the CIE L*a*b* color space of the raw organic colouring substance are measured as follows.

The substance is compacted in a rectangular cup having dimensions of 2×1.5 cm and a depth of 3 mm, by applying a pressure of 100 bars.

The a* and b* values of the compacted substance are measured with a Minolta 3700d spectrophotometer, in mode specular excluded, under illuminant D65, medium aperture.

The color values a* and b* of the raw composite pigment are also measured with the same spectrophotometer under the same illumination conditions in a cup having the same dimensions as above, in a compacted state with the pressure of 100 bars.

The at least one composite pigment may optionally comprise at least one binder to fix the at least one organic coloring substance to the inorganic core.

The present disclosure makes it possible to benefit from cosmetic compositions comprising at least one composite pigment that has both relatively strong covering power and the benefits of an organic coloring substance, such as relatively high colour saturation.

The composite pigment may have a density higher than that of the organic coloring substance alone, on account of the presence of the inorganic core, the density of the said core possibly being higher than that of the organic coloring substance.

A suitable shade may be obtained by mixing composite pigments according to the present disclosure, or alternatively by mixing organic coloring substances into the composite pigment or with successive layers of binders and organic coloring substances in the composite pigment.

The organic coloring substance may be chosen from particulate compounds that are insoluble in the physiologically acceptable medium of the composition.

The term "physiologically acceptable medium" denotes a non-toxic medium that may be applied to human skin, lips or integuments. The physiologically acceptable medium will be adapted to the nature of the support onto which the composition is to be applied, and also to the form in which the composition is intended to be packaged, especially solid, semi-solid or fluid at room temperature and atmospheric pressure.

The term "cosmetic composition" denotes a composition as defined in Directive 93/35/EEC of the Council of 14 Jun. 1993.

The binder may be of any type provided that it allows the organic coloring substance to adhere to the surface of the inorganic core.

In one embodiment, the binder may comprise an organic binder, for example a silicone polymer.

Among the binders that may be used in the composition of the present disclosure, non-limiting mention may be made of binders chosen from silicone compounds, silicone polymers, polymeric or oligomeric compounds or the like, such as alkoxysilanes, fluoroalkylsilanes and polysiloxanes, and also various couplers, such as couplers based on silane, on titanates, on aluminates or on zirconates, and mixtures thereof.

Among the materials that may be used for the inorganic core, non-limiting mention may be made of metal salts and metal oxides, such as oxides of titanium, zirconium, cerium, zinc, iron, ferric blue and chromium, as well as barium sulphate, aluminas, glasses, ceramics, graphite, silicas, silicates, such as aluminosilicates and borosilicates, and synthetic mica, and mixtures thereof.

In one embodiment of the present disclosure, titanium oxides $TiO_2$ and iron oxides $Fe_2O_3$ may be used as materials for the inorganic core.

The organic coloring substance may be present in the composition in an amount ranging from 1 to 500 parts by weight per 100 parts by weight of the core, for example.

In some exemplary embodiments, the size of the composite pigment particles may be less than 1 μm. In embodiments of the present disclosure, the size of the composite pigment particles may range from 5 nm to 100 nm. In one embodiment, the size of the composite pigment particles may range from 5 nm to 75 nm. In another embodiment, the size of the composite pigment particles may range from 15 nm to 40 nm.

The term "size" denotes the dimension given by the statistical particle-size distribution to half of the population, known as the D50.

The composite pigment particles may have varied forms. These particles may be in the form of platelets or globules, for example in spherical form, and may be hollow or solid. The expression "in the form of platelets" denotes particles in which the ratio of the largest dimension to the thickness is greater than or equal to 5.

The composition may comprise only composite pigments as defined above or, as a variant, comprise composite pigments and also pigments having another structure, such as mineral pigments, interference pigments or organic coloring substances, for example lakes. In some exemplary embodiments, the composition may be free of uncoated $TiO_2$ particles.

The composition may comprise at least one composite pigment in an amount ranging from 0.1% and 20% by weight relative to the total weight of the composition. In one embodiment, the at least one composite pigment may be present in an amount ranging from 0.1% to 15% by weight relative to the total weight of the composition. In a further embodiment, the at least one composite pigment may be present in an amount ranging from 0.5% to 10% by weight relative to the total weight of the composition.

The composition may comprise at least one aqueous or organic solvent.

When the composition comprises at least one organic solvent, these solvents may be present in an amount ranging from 0 to 99% relative to the total weight of the composition.

The amount of the at least one solvent, such as the at least one organic solvent, can depend on the nature of the support onto which the composition is intended to be applied.

In the case of a nail varnish, for example, the organic solvent may be present in the composition in an amount ranging, for example, from 30% to 99% by weight relative to the total weight of the composition. In one embodiment, the organic solvent may be present in an amount ranging from 60% to 90% by weight relative to the total weight of the composition.

Among organic solvents that may be used in the composition according to the present disclosure, non-limiting mention may be made:

ketones that are liquid at room temperature, such as methyl ethyl ketone, methyl isobutyl ketone, diisobutyl ketone, isophorone, cyclohexanone or acetone;

alcohols that are liquid at room temperature, such as ethanol, isopropanol, diacetone alcohol, 2-butoxyethanol or cyclohexanol;

glycols that are liquid at room temperature, such as ethylene glycol, propylene glycol, pentylene glycol or glycerol;

propylene glycol ethers that are liquid at room temperature, such as propylene glycol monomethyl ether, propylene glycol monomethyl ether acetate or dipropylene glycol mono-n-butyl ether;

short-chain esters (containing from 3 to 8 carbon atoms in total) such as ethyl acetate, methyl acetate, propyl acetate, n-butyl acetate or isopentyl acetate; and alkanes that are liquid at room temperature, such as decane, heptane, dodecane or cyclohexane.

The composition may also comprise water or a mixture of water and hydrophilic organic solvents commonly used in cosmetics, for instance alcohols including linear or branched lower monoalcohols containing from 2 to 5 carbon atoms, such as ethanol, isopropanol or n-propanol, or polyols, such as glycerol, digylcerol, propylene glycol, sorbitol, pentylene glycol or polyethylene glycols. The composition may also contain hydrophilic $C_2$ ethers and $C_2$-$C_4$ aldehydes. Water or a mixture of water and of hydrophilic organic solvents may be present in the composition in an amount ranging, for example, from 0% to 90%, such as 0.1% to 90% by weight relative to the total weight of the composition. In one embodiment, the water or a mixture of water and of hydrophilic organic solvents may be present in an amount ranging from 0% to 60% by weight relative to the total weight of the composition. In another embodiment, the water or mixture of water and hydrophilic organic solvents may be present in an amount ranging from 0.1% to 60% by weight relative to the total weight of the composition.

The composition, especially when it is intended to be applied to the lips, may comprise a fatty phase such as at least one fatty substance that is liquid at room temperature (25° C.) and/or a fatty substance that is solid at room temperature, such as waxes, pasty fatty substances, and gums, and mixtures thereof. The fatty phase may also contain lipophilic organic solvents.

The composition may have, for example, a continuous fatty phase, which may contain less than 5% water, such as less than 1% water relative to its total weight. The continuous fatty phase may be in anhydrous form.

As fatty substances that are liquid at room temperature, often referred to as "oils", non-limiting mention may be made of: hydrocarbon-based plant oils such as liquid triglycerides of fatty acids of 4 to 10 carbon atoms such as heptanoic or octanoic acid triglycerides; or sunflower oil; maize oil; soybean oil; grapeseed oil; sesame seed oil; apricot oil; macadamia oil; castor oil; avocado oil; caprylic/capric acid triglycerides; jojoba oil; shea butter; linear or branched hydrocarbons of mineral or synthetic origin, such as liquid paraffins and derivatives thereof, petroleum jelly, polydecenes, and hydrogenated polyisobutene such as parleam; synthetic esters and ethers, such as fatty acids including purcellin oil, isopropyl myristate, 2-ethylhexyl palmitate, 2-octyldodecyl stearate, 2-octyldodecyl erucate or isostearyl isostearate; isononyl isonanoate; hydroxylated esters, such as isostearyl lactate, octyl hydroxystearate, octyldodecyl hydroxystearate, diisostearyl malate, triisocetyl citrate or fatty alkyl heptanoates, octanoates and decanoates; polyol esters, for instance propylene glycol dioctanoate, neopentyl glycol diheptanoate or diethylene glycol diisononanoate; and pentaerythritol esters; fatty alcohols containing from 12 to 26 carbon atoms, for instance octyldodecanol, 2-butyloctanol, 2-hexyldecanol, 2-undecylpentadecanol or oleyl alcohol; partially hydrocarbon-based and/or silicone-based fluoro oils; silicone oils, for instance volatile or non-volatile, linear or cyclic polymethylsiloxanes (PDMSs) that are liquid or pasty at room temperature, for instance cyclomethicones, dimethicones, optionally comprising a phenyl group, such as phenyl trimethicones, phenyltrimethylsiloxydiphenylsiloxanes, diphenylmethyldimethyltrisiloxanes, diphenyl dimethicones, phenyl dimethicones and polymethylphenylsiloxanes; and mixtures thereof. The oils may be present in an amount ranging from 0.01% to 90%, such as from 0.1% to 85% by weight, relative to the total weight of the composition.

The pasty fatty substances can be hydrocarbon-based compounds with a melting point ranging from 25 to 60° C., such as from 30 to 45° C., and/or a hardness ranging from 0.001 and 0.5 Mpa, such as from 0.005 to 0.4 MPa, for instance lanolins and derivatives thereof.

The waxes may be solid at room temperature (25° C.), with a reversible solid/liquid change of state, having a melting point of greater than 30° C. which may be up to 200° C., a hardness of greater than 0.5 MPa, and having in solid form an anisotropic crystal organization. In one embodiment, the waxes may have a melting point of greater than 25° C., such as greater than 45° C. The waxes may be hydrocarbon-based waxes, fluoro waxes and/or silicone waxes and may be of plant, mineral, animal and/or synthetic origin. As waxes that may be used, non-limiting mention may be made of beeswax, carnauba wax or candelilla wax, paraffin, microcrystalline waxes, ceresin or ozokerite; synthetic waxes, such as polyethylene wax or Fischer-Tropsch wax, and silicone waxes, for instance alkyl- or alkoxydimethicones containing from 16 to 45 carbon atoms. The composition may contain from 0 to 50% by weight of waxes, or from 1% to 30% by weight of waxes, relative to the total weight of the composition.

In some exemplary embodiments, the composition may contain an oil of high molar mass ranging from 650 to 10,000 g/mol. The expression "oil" is understood to mean a non-aqueous compound which is immiscible with water, and which is liquid at room temperature (25° C.) and atmospheric pressure (760 mmHg).

The oil may have a molar mass ranging from 650 to 10,000 g/mol, and can, for example, range from 750 and 7,500 g/mol.

An oil having a molar mass ranging from 650 to 10,000 g/mol may be chosen from:
lipophilic polymers such as:
  polybutylenes such as INDOPOL H-100 (having a molar mass or MM=965 g/mol), INDOPOL H-300 (MM=1 340 g/mol), INDOPOL H-1500 (MM=2 160 g/mol) which are marketed or manufactured by the company AMOCO,
  hydrogenated polyisobutylenes such as PANALANE H-300 E which are marketed or manufactured by the company AMOCO (M=1,340 g/mol), VISEAL 20000 marketed or manufactured by the company SYNTEAL (MM=6,000 g/mol), REWOPAL PIB 1000 marketed or manufactured by the company WITCO (MM=1,000 g/mol),
  polydecenes and hydrogenated polydecenes such as: PURESYN 10 (MM=723 g/mol), PURESYN 150 (MM=9,200 g/mol) which are marketed or manufactured by the company MOBIL CHEMICALS,
  copolymers of vinypyrrolidone such as: the vinylpyrolidone/1-hexadecene copolymer, ANTARON V-216, marketed or manufactured by the company ISP (MM=7,300 g/mol),
esters such as:
  linear fatty acid esters having a total number of carbons ranging from 35 to 70 such as pentaerythrityl tetrapelargonate (MM=697.05 g/mol),
  hydroxylated esters such as 2-polyglyceryl triisostearate (MM=965.58 g/mol),
  aromatic esters such as tridecyl trimellitate (MM=757.19 g/mol),
  $C_{24}$-$C_{28}$ branched fatty acid or fatty alcohol esters such as those described in European Patent Application No. EP-A-0 955 039, including triisoarachidyl citrate (MM=1033.76 g/mol), pentaerythrityl tetraisononanoate (MM=697.05 g/mol), glyceryl triisostearate (MM=891.51 g/mol), glyceryl tri(2-decyltetradecanoate) (MM=1143.98 g/mol), pentaerythrityl tetraisostearate (MM=1202.02 g/mol), polyglyceryl-2 tetraisostearate (MM=1232.04 g/mol) or alternatively pentaerythrityl tetra(2-decyltetradecanoate) (MM=1538.66 g/mol),
silicone oils such as phenylated silicone such as BELSIL PDM 1000 from the company WACKER (MM=9,000 g/mol), polyesters and esters obtained from dimer diol, such as for example esters of dimer diol and fatty acid, and esters from dimer diol and dimer diacid. For example esters of dilinoeic acid and dilinoleic diol sold by NIPPON FINE CHEMICAL under the name LUSPLAN DD-DA5® et DD-DA7®. These oils are described in detail in U.S. Patent Application No. U.S. 2004-0175338, which content is incorporated herewith by reference, oils of plant origin such as sesame oil (820.6 g/mol), and mixtures thereof.

In some embodiments, the oil having a molar mass ranging from 650 to 10,000 g/mol may be present in an amount ranging from 1 to 99% by weight relative to the total weight of the composition. In one embodiment, the oil having a molar mass ranging from 650 to 10,000 g/mol may be present in an amount ranging from 10 to 80% by weight relative to the total weight of the composition. In another embodiment, the oil having a molar mass ranging from 650 to 10,000 g/mol may be present in an amount ranging from 5 to 70% by weight relative of the total weight of the composition.

The gums that may be used can be high molecular weight polydimethylsiloxanes (PDMSs) or cellulose gums or polysaccharides.

The composition may also comprise, for example, a film-forming polymer, such as in the case of a mascara or a nail varnish. The term "film-forming polymer" denotes a polymer capable, by itself or in the presence of an auxiliary film-forming agent, of forming a continuous film that adheres to a support and especially to keratin materials.

Among the film-forming polymers that may be used in a composition according to the present disclosure, non-limiting mention may be made of synthetic polymers, of free-radical type or of polycondensate type, polymers of natural origin, such as nitrocellulose or cellulose esters, and mixtures thereof.

The film-forming polymers of free-radical type may especially be vinyl polymers or copolymers, such as acrylic polymers.

The vinyl film-forming polymers may result from the polymerization of ethylenically unsaturated monomers containing at least one acid group and/or esters of these acidic monomers and/or amides of these acidic monomers, for instance α,β-ethylenic unsaturated carboxylic acids such as acrylic acid, methacrylic acid, crotonic acid, maleic acid or itaconic acid.

The vinyl film-forming polymers may also result from the homopolymerization or copolymerization of monomers chosen from vinyl esters, for instance vinyl acetate, vinyl neodecanoate, vinyl pivalate, vinyl benzoate and vinyl t-butylbenzoate, and styrene monomers, for instance styrene and α-methylstyrene.

Among the film-forming polycondensates that may be used in the composition of the present disclosure, non-limiting mention may be made of polyurethanes, polyesters, polyesteramides, polyamides and polyureas.

The optionally modified polymers of natural origin may be chosen from shellac resin, sandarac gum, dammar resins, elemi gums, copal resins, cellulose-based polymers, such as nitrocellulose, ethylcellulose or nitrocellulose esters chosen, for example, from cellulose acetate, cellulose acetobutyrate and cellulose acetopropionate, and mixtures thereof.

The film-forming polymer may be present in the form of particles in aqueous or oily dispersion, generally known as latices or pseudolatices. The film-forming polymer may comprise one or more stable dispersions of particles of generally spherical polymers of one or more polymers, in a physiologically acceptable liquid fatty phase. These dispersions are generally known as polymer NADs (Non-Aqueous Dispersions), as opposed to latices, which are aqueous polymer dispersions. These dispersions may especially be in the form of polymer nanoparticles in stable dispersion in the said fatty phase. In one embodiment, the nanoparticles range from 5 to 600 nm in size. The techniques for preparing these dispersions are well known to those skilled in the art.

Aqueous dispersions of film-forming polymers that may be used include the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® by the company Daito Kasei Kogyo; or the aqueous polyurethane dispersions sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulphopolyesters sold under the brand name Eastman AQ by the company Eastman Chemical Products.

The composition according to the present disclosure may also comprise an auxiliary film-forming agent that promotes the formation of a film with the film-forming polymer.

The composition may also comprise fillers. The term "fillers" denotes particles of any form, which are insoluble in the medium of the composition, irrespective of the temperature at which the composition is manufactured. These fillers may serve to modify the rheology or texture of the composition. The nature and amount of the solid substances depend on the desired mechanical properties and textures.

Non-limiting examples of fillers that may be mentioned include talc, mica, silica, kaolin, sericite, polyamide powder, polyethylene powder, polytetrafluoroethylene powder, polymethyl methacrylate powder, polyurethane powder, starch powders and silicone resin beads.

The composition may comprise at least one cosmetic or dermatological active agent. As cosmetic, dermatological, hygiene or pharmaceutical active agents that may be used in the compositions of the present disclosure, non-limiting mention may be made of moisturizers (polyols, for instance glycerol), vitamins (C, A, E, F, B or PP), essential fatty acids, essential oils, ceramides, sphingolipids, liposoluble sunscreens or sunscreens in the form of nanoparticles, and specific skin-treating active agents (protective agents, antibacterial agents, anti-wrinkle agents, etc.). These active agents may be used, for example, in amounts ranging from 0 to 20%, such as from 0.001 to 15% by weight, relative to the total weight of the composition.

The cosmetic composition may also contain ingredients commonly used in cosmetics, for instance thickeners, surfactants, trace elements, moisturizers, softeners, sequestering agents, fragrances, acidifying or basifying agents, preserving agents, antioxidants, UV-screening agents or dyes, or mixtures thereof.

The cosmetic composition may also comprise, depending on the type of application envisaged, constituents conventionally used in the fields under consideration, which are present in an amount that is suitable for the desired presentation form.

The composition may be in various forms, depending on its intended use. The cosmetic composition may thus be in any presentation form normally used for topical application and especially in anhydrous form, in the form of an oily or aqueous solution, an oily or aqueous gel, an oil-in-water, water-in-oil, wax-in-water or water-in-wax emulsion, a multiple emulsion, or a dispersion of oil in water by means of vesicles located at the oil/water interface.

The composition may be in the form of a cast product, such as in the form of a stick in the case of a lipstick or a lipcare product.

The composition may also be in various other forms, for example in the form of a more or less viscous liquid, a gel or a paste.

The composition may also be in the form of a semi-solid or a solid, for example a cake to be moistened at the time of use, so as to allow it to be disintegrated.

The cosmetic composition may constitute, inter alia, a lipstick, a liquid gloss, a lipstick paste, a makeup rouge, a lip pencil, a solid or fluid foundation, a concealer product or eye-contour product, an eyeliner, a mascara, a nail varnish, an eyeshadow, a body or hair makeup product or an antisun product or skin-coloring product.

An aspect of the present disclosure is thus also a liquid or semi-solid lipstick comprising a composition as defined above.

Another aspect of the present disclosure is also a foundation comprising a composition as defined above.

A further aspect of the present disclosure is also a nail varnish comprising a composition as defined above.

Another aspect of the present disclosure is also a mascara comprising a composition as defined above.

Yet another aspect of the present disclosure is also a product for dyeing hair fibers, comprising a composition as defined above.

A further aspect of the present disclosure is also the use of a composition as defined above for making up the skin, the lips or the integuments.

Composite Pigment

The composite pigment may be composed especially of particles comprising:
an inorganic core at least partially covered with at least one organic coloring substance, and
at least one binder for fixing the at least one organic coloring substance onto the core.

The composite pigments may have, for example, a BET specific surface area ranging from 0.5 and 500 m$^2$/g, such as from 1.5 to 400 m$^2$/g, or from 2 to 300 m$^2$/g. The "BET specific surface area" is the value measured by the BET (Brunauer-Emmaett-Telles) method.

The saturation C* of the composite pigment may be above about 30, measured according to the following protocol.

Protocol for Measuring the Saturation C* of the Composite Pigment:

The color values a* and b* in the CIE L*a*b* colorspace of the composite pigment are measured as follows.

The composite pigment in a raw state is compacted in a rectangular cup having dimensions of 2×1.5 cm and a depth of 3 mm, by applying a pressure of 100 bars.

The a* and b* values of the compacted pigment are measured with a Minolta 3700 spectrophotometer, in mode specular excluded, with illuminant D65, medium aperture. The saturation is computed as $C^*=(a^{*2}+b^{*2})^{1/2}$.

Inorganic Core

The inorganic core may have any form that is suitable for fixing particles of organic coloring substance, wherein non-limiting examples include spherical, globular, granular, polyhedral, acicular, spindle-shaped, flattened in the form of a flake, a rice grain, or a scale, and a combination of these forms.

In one embodiment, the ratio of the largest dimension of the core to its smallest dimension is in the range 1 to 50.

The inorganic core may have a mean size ranging from 1 nm (nanometer) to 100 nm, such as in the range from 5 nm to 75 nm, or in the range from 10 nm to 50 nm. In one embodiment, the inorganic core may have a mean size ranging from 15 nm to 40 nm, such as, for example, 20 nm or 25 nm.

The term "mean size" means the dimension given by the statistical grain size distribution curve at 50% population, termed D50. The mean size may be a number average determined by image analysis (electron microscopy).

The inorganic core may present a refractive index not less than 2, better not less than 2.1, for example not less than 2.2.

Among materials that form the inorganic core, non-limiting mention may be made of metallic salts and metal oxides, such as oxides of titanium, zirconium, cerium, zinc, iron, iron blue, aluminum, and chromium, aluminas, glasses, ceramics, graphite, silicas, silicates, including aluminosilicates and borosilicates, synthetic mica, and mixtures thereof.

In one embodiment, the inorganic core may be formed from oxides of titanium, such as $TiO_2$, iron, such as $Fe_2O_3$, cerium, zinc, and aluminum; silicas; and silicates, such as aluminosilicates and borosilicates.

The inorganic core may have a specific surface area, measured using the BET method, in the range from about 1 m$^2$/g to about 1000 m$^2$/g, such as in the range from about 10 m$^2$/g to about 600 m$^2$/g, or in the range from about 20 m$^2$/g to about 400 m$^2$/g. In one embodiment, the inorganic core may have a specific surface area ranging from 25 m$^2$/g to 75 m$^2$/g. In another embodiment, the inorganic core may have a specific surface area ranging from 40 m$^2$/g to 60 m$^2$/g, such as, for example, 50 m$^2$/g.

The inorganic core may be colored if appropriate.

The mass proportion of the core in the composite pigment may exceed 50% relative to the total weight of the composite pigment. For example, the core may be present in the composite pigment in an amount ranging from 50% to 70% by weight relative to the total weight of the composite pigment, such as from 60 to 70% by weight relative to the total weight of the composite pigment.

Binder

The binder when present may be of any type provided that it allows the organic coloring substance to adhere to the surface of the inorganic core. The binder may be organic.

The binder may be chosen from non-limiting examples including silicone compounds, such as silicone polymers, polymeric or oligomeric compounds or the like, and from organosilanes, fluoroalkyl organosilanes and polysiloxanes, and also various couplers, such as couplers based on silanes, on titanates, on aluminates or on zirconates, and mixtures thereof.

In one embodiment, the silicone compound may be chosen from:
the organosilanes (1) obtained from alkoxysilanes,
the modified or unmodified polysiloxanes (2) chosen from a non-limiting list comprising:
the modified polysiloxanes (2A) comprising at least one radical chosen especially from polyethers, polyesters and epoxy compounds (these will be referred to as "modified polysiloxanes"),
the polysiloxanes (2B) bearing, on a silicon atom located at the end of the polymer, at least one group chosen from a non-limiting list comprising carboxylic acids, alcohols and hydroxyl groups, and
the fluoroalkyl organosilane compounds (3) obtained from fluoroalkylsilanes.

The organosilane compounds (1) may be obtained from alkoxysilane compounds of formula (I):

  (I)

wherein:
R$^1$ is chosen from C$_6$H$_5$—, (CH$_3$)$_2$ CH CH$_2$— and n-C$_b$H$_{2b+1}$— (wherein b ranges from 1 to 18),
X is chosen from CH$_3$O— and C$_2$H$_5$O—, and
a ranges from 0 to 3.

Non-limiting examples of alkoxysilane compounds may include alkoxysilanes chosen from: methyltriethoxysilane, dimethyldiethoxysilane, phenyltriethyoxysilane, diphenyldiethoxysilane, methyltrimethoxysilane, dimethyldimethoxysilane, phenyltrimethoxysilane, diphenyldimethoxysilane, isobutyltrimethoxysilane, decyltrimethoxysilane and the like. In one embodiment, the alkoxysilane compounds may be chosen from methyltriethoxysilane, phenyltriethyoxysilane, methyltrimethoxysilane, dimethyldimethoxysilane and isobutyltrimethoxysilane. In a further embodiment, the alkoxysilane compounds may be chose from methyltriethoxysilane, methyltrimethoxysilane and phenyltriethyoxysilane.

The polysiloxanes (2) may be chosen from compounds of formula (II):

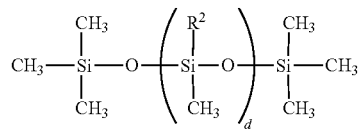  (II)

wherein
R$^2$ is chosen from H— and CH$_3$— and
d ranges from 15 to 450.

In one embodiment, R$^2$ comprises H.

The modified polysiloxanes (2A) may be chosen from the following formulae:
(a$^1$) modified polysiloxanes bearing polyethers, chosen from compounds of formula (III)

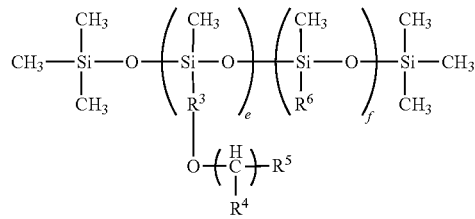  (III)

wherein
R$^3$ comprises —(CH$_2$)$_h$—;
R$^4$ comprises —(CH$_2$)$_i$—CH$_3$;
R$^5$ is chosen from —OH, —COOH, —CH═CH$_2$, —C(CH$_3$)═CH$_2$ and —(CH$_2$)$_j$—CH$_3$;
R$^6$ comprises —(CH$_2$)$_k$—CH$_3$;
g and h independently range from 1 to 15;
j and k independently range from 0 to 15;
e ranges from 1 to 50; and
f ranges from 1 to 300;
(a$^2$) modified polysiloxanes bearing polyesters, chosen from compounds of formula (IV):

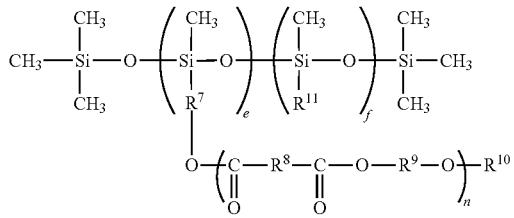  (IV)

wherein
R$^7$, R$^8$ and R$^9$ are independently chosen from —(CH$_2$)$_q$—;
R$^{10}$ is chosen from —OH, —COOH, —CH═CH$_2$, —C(CH$_3$)═CH$_2$ and —(CH$_2$)$_r$—CH$_3$;
R$^{11}$ comprises —(CH$_2$)$_s$—CH$_3$;
n and q independently range from 1 to 15;
r and s independently range from 0 to 15;
e ranges from 1 to 50; and
f ranges from 1 to 300;
(a$^3$) modified polysiloxanes bearing epoxy radicals, chosen from compounds of formula (V):

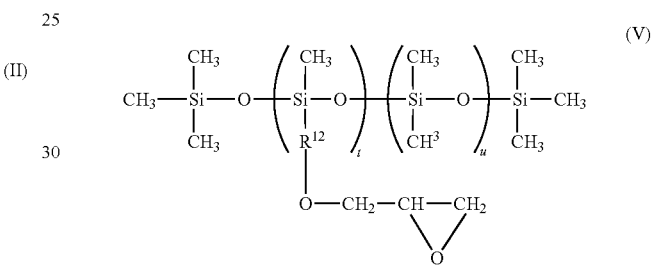  (V)

wherein
R$^{12}$ comprises —(CH$_2$)$_v$—;
v ranges from 1 to 15;
t ranges from 1 to 50; and
u ranges from 1 to 300; and
mixtures thereof.

In one embodiment, the modified polysiloxanes (2A) comprise modified polysiloxanes bearing polyethers of formula (III).

The polysiloxanes modified on the end portion (2B) may be chosen from compounds of formula (VI):

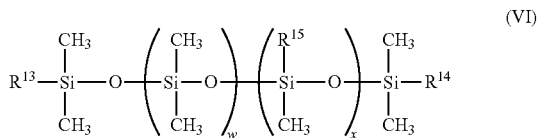  (VI)

wherein
R$^{13}$ and R$^{14}$ are independently chosen from —OH, R$^{16}$ OH and R$^{17}$ COOH;
R$^{15}$ is chosen from —CH$_3$ and —C$_6$H$_5$;
R$^{16}$ and R$^{17}$ comprise —(CH$_2$)$_y$—;
y ranges from 1 to 15;
w ranges from 1 to 200; and
x ranges from 0 to 100.

In one embodiment, the polysiloxanes modified on at least one end, comprise polysiloxanes bearing at least radical R$^{16}$ and/or R$^{17}$ bearing a carboxylic acid group on at least one terminal silicon atom.

The fluoroalkyl organosilane compounds (3) may be obtained from fluoroalkyl silanes of formula (VII):

$$CF_3(CF_2)_zCH_2CH_2(R^{18})_aSiX_{4-a} \quad (VII)$$

wherein:
R$^{18}$ is chosen from CH$_3$—, C$_2$H$_5$—, CH$_3$O— and C$_2$H$_5$O—;
X is chosen from CH$_3$O— and C$_2$H$_5$O—;
z ranges from 0 to 15; and
a ranges from 0 to 3.

The fluoroalkyl silanes may be chosen from non-limiting examples including trifluoropropyltrimethoxysilane, tridecafluorooctyltrimethoxysilane, heptadecafluorodecyltrimethoxysilane, heptadecafluorodecylmethyldimethoxysilane, trifluoropropyltriethoxysilane, tridecafluorooctyltriethoxysilane, heptadecafluorodecyltriethoxysilane, heptadecafluorodecylmethyldiethoxysilane and the like. In one embodiment, the fluoroalkyl silanes are chosen from trifluoropropyltrimethoxysilane, tridecafluorooctyltrimethoxysilane and heptadecafluorodecyltrimethoxysilane. In a further embodiment, the fluoroalkyl silanes are chosen from trifluoropropyltrimethoxysilane and tridecafluorooctyltrimethoxysilane.

The silane-based couplers may be chosen from non-limiting examples including vinyltrimethoxysilane, vinyltriethoxysilane, γ-aminopropyltriethoxysilane, γ-glycidoxypropyltrimethoxysilane, γ-mercaptopropyltrimethoxysilane, γ-methacryloxypropyltrimethoxysilane, N-β-(aminoethyl)-γ-aminopropyltrimethoxysilane, γ-glycidoxypropylmethyldimethoxysilane and γ-chloropropyltrimethoxysilane, and the like.

The titanate-based couplers may be chosen from isopropylstearoyl titanate, isopropyltris(dioctyl pyrophosphate) titanate, isopropyltris(N-aminoethylaminoethyl) titanate, tetraoctylbis(ditridecyl phosphate) titanate, tetrakis(2,2-diaryloxymethyl-1-butyl)bis(ditridecyl)phosphate titanate, bis(dioctyl pyrophosphate)oxyacetate titanate and bis(dioctyl pyrophosphate)ethylene titanate, and the like.

The aluminate-based couplers may be chosen from acetoalkoxyaluminium diisopropoxide, aluminium diisopropoxymonoethylacetoacetate, aluminium trisethylacetoacetate and aluminium trisacetylacetonate, and the like.

The zirconate-based couplers may be chosen from zirconium tetrakisacetylacetonate, zirconium dibutoxybisacetylacetonate, zirconium tetrakisethylacetoacetate, zirconium tributoxymonoethylacetoacetate and zirconium tributoxyacetylacetonate, and the like.

The compounds used as binder may have a molecular mass ranging from 300 to 100,000.

In order to obtain a coat that covers the inorganic cores uniformly, the binder may be in a form that is liquid or soluble in water or in various solvents.

The amount of binder may range from 0.01 to 15%, such as from 0.02% to 12.5% or 0.03 to 10% by weight (calculated relative to C or Si) relative to the weight of the particles comprising the core and the binder. For further details regarding the way of calculating the relative amount of the binder, reference may be made to European Patent Application No. EP 1 184 426 A2.

In one embodiment, the amount of the binder present in the composition may not exceed 5%, or for example 3%, by weight of the total weight of the composite pigment.

Organic Coloring Substance

The organic coloring substance may, for example, comprise at least one organic coloring substance, for example at least one organic lake or other organic pigment.

The organic coloring substance may, for example, be selected from particular compounds that are insoluble in the physiologically acceptable medium of the composition.

The organic coloring substance may, for example, comprise pigments, for example organic lakes or other pigments, which may be selected from the following compounds and mixtures thereof:
cochineal carmine;
the organic coloring substances of azo, anthraquinone, indigo, xanthene, pyrene, quinoline, triphenylmethane, or fluorane dyes; and
organic lakes or insoluble salts of sodium, potassium, calcium, barium, aluminum, zirconium, strontium, titanium, or of acid dyes such as azo, anthraquinone, indigo, xanthene, pyrene, quinoline, triphenylmethane, or fluorine dyes, which dyes may comprise at least one carboxylic or sulfonic acid group.

Among organic coloring substances that may be used in the composition according to the present disclosure, non-limiting mention may be made of D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, and FD&C Yellow No. 6.

The organic coloring substance may comprise an organic lake supported by an organic support such as colophon or aluminum benzoate, for example.

Among organic lakes that may be used in the composition according to the present disclosure, non-limiting mention may be made of D&C Red No. 2 Aluminum lake, D&C Red No. 3 Aluminum lake, D&C Red No. 4 Aluminum lake, D&C Red No. 6 Aluminum lake, D&C Red No. 6 Barium lake, D&C Red No. 6 Barium/Strontium lake, D&C Red No. 6 Strontium lake, D&C Red No. 6 Potassium lake, D&C Red No. 7 Aluminum lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminum lake, D&C Red No. 9 Barium lake, D&C Red No. 9 Barium/Strontium lake, D&C Red No. 9 Zirconium lake, D&C Red No. 10 Sodium lake, D&C Red No. 19 Aluminum lake, D&C Red No. 19 Barium lake, D&C Red No. 19 Zirconium lake, D&C Red No. 21 Aluminum lake, D&C Red No. 21 Zirconium lake, D&C Red No. 22 Aluminum lake, D&C Red No. 27 Aluminum lake, D&C Red No. 27 Aluminum/Titanium/Zirconium lake, D&C Red No. 27 Barium lake, D&C Red No. 27 Calcium lake, D&C Red No. 27 Zirconium lake, D&C Red No. 28 Aluminum lake, D&C Red No. 30 lake, D&C Red No. 31 Calcium lake, D&C Red No. 33 Aluminum lake, D&C Red No. 34 Calcium lake, D&C Red No. 36 lake, D&C Red No. 40 Aluminum lake, D&C Blue No. 1 Aluminum lake, D&C Green No. 3 Aluminum lake, D&C Orange No. 4 Aluminum lake, D&C Orange No. 5 Aluminum lake, D&C Orange No. 5 Zirconium lake, D&C Orange No. 10 Aluminum lake, D&C Orange No. 17 Barium lake, D&C Yellow No. 5 Aluminum lake, D&C Yellow No. 5 Zirconium lake, D&C Yellow No. 6 Aluminum lake, D&C Yellow No. 7 Zirconium lake, D&C Yellow No. 10 Aluminum lake, FD&C Blue No. 1 Aluminum lake, FD&C Red No. 4 Aluminum lake, FD&C Red No. 40 Aluminum lake, FD&C Yellow No. 5 Aluminum lake, and FD&C Yellow No. 6 Aluminum lake.

The chemical compounds corresponding to each of the organic coloring substances listed above are mentioned in the work entitled "International Cosmetic Ingredient Dictionary and Handbook", 1997 edition, pages 371 to 386 and 524 to 528, published by "The Cosmetic, Toiletry, and Fragrance Association", the contents of which are hereby incorporated by reference.

The organic coloring substance may be present in the composition in an amount ranging from 10 parts to 500 parts by weight per 100 parts of inorganic core. In other embodiments of the present disclosure, the organic coloring substance may be present in the composition in an amount ranging from 20 parts to 250 parts by weight or from 40 parts to 125 parts by weight per 100 parts of inorganic core.

The proportion of the organic coloring substance in the composite pigment may exceed 30% relative to the total weight of the composite pigment. In one embodiment, the organic coloring substance may be present in the composite pigment in an amount ranging from 30% to 50%, such as from 30% to 40%.

Preparation of the Composite Pigment

The composite pigment may be manufactured by any appropriate method, for example a mechano-chemical method or a method of precipitation in solution, with dissolution of an organic coloring substance and a precipitation thereof at the surface of the core.

A binder may or may not be used.

A method comprising a mechanical mixing of the organic coloring substance and the core is preferred. A binder may be added and mixed with the core before the introduction of the organic coloring substance.

The composite pigment may, for example, be produced using one of the processes described in European Patent Applications EP 1 184 426 and EP 1 217 046, the contents of which are hereby incorporated by reference. In one embodiment, the process described in EP 1 184 426 is used to produce the composite pigment.

In one implementation, the particles intended to constitute the inorganic core are first mixed with the binder.

So that the binder can adhere uniformly to the surface of the inorganic core, it is preferable to pass said particles initially through a mill to disaggregate them.

The mixing and agitation conditions can be selected so that the core is uniformly coated with binder. Such conditions may be controlled so that the linear load is in the range 19.6 N/cm (newtons/centimeter) to 19160 N/cm, such as in the range 98 N/cm to 14170 N/cm or 147 N/cm to 980 N/cm. The treatment time may range from 5 minutes to 24 hours. In one embodiment, the treatment time ranges from 10 minutes to 20 hours. The rotation rate may range from 2 rpm (revolutions per minute) to 1000 rpm. In one embodiment, the rotation rate may range from 5 rpm to 1000 rpm, and in a further embodiment, the rotation rate may range from 10 rpm to 800 rpm.

After at least partially coating the inorganic core with binder, the organic coloring substance can be added and mixed with agitation so that it adheres to the layer of binder.

Examples of addition methods are continuous addition in large quantities, or in small quantities.

Mixing and agitation, whether of the inorganic cores with the binder or of the organic coloring substance with the inorganic cores coated with binder, may be carried out using an apparatus which can apply a sharp shearing and/or compressive force to the mixture of powders. Examples of apparatus of that type are roller mixers, blade mixers, and the like. In one embodiment, roller mixers are used. Examples of apparatus that may be used are taught in European Patent No. EP 1 184 426 A2.

Another method for manufacturing a composite pigment has been described in Japanese Patent No. JP 3286463, which discloses a solution precipitation process.

The organic coloring substance can be dissolved in ethanol and the inorganic cores then dispersed in the ethanolic solution.

An aqueous alkaline solution of sodium or potassium carbonate can then be slowly added to these mixtures and finally, an ethanolic calcium chloride solution can be slowly added, with constant agitation.

PROPOSED EXAMPLES

Cosmetic compositions comprising composite pigments with the formulations below may be prepared, these compositions being prepared according to the preparation processes conventionally used in cosmetics.

In the examples, the proportions are in weight relative to the total weight.

Example 1

Lipstick

| | |
|---|---|
| Microcrystalline wax | 2% |
| Ozokerite | 5% |
| Candelilla wax | 7% |
| Carnauba wax | 3% |
| Capric/caprylic acid triglycerides | 18% |
| Octyldodecanol | 10% |
| Lanolin oil | 6% |
| Acetylated lanolin oil | 6% |
| Composite pigment* | 9% |
| Fragrance | 0.5% |
| Castor oil | ql 100% |

*Mixture synthetic titanium dioxide**, D&C RED 7, polymethylhydrogensiloxane (respective weight proportions $TiO_2$: 65.8/D&C RED 7: 32.9/binder: 1.3)
**$TiO_2$ having BET specific surface of 50 $m^2$/g and a mean size of 20 nm.

Example 2

Foundation

| Oily phase | |
|---|---|
| Surfactant sold under the trade name "Abil WE 09" by the company Goldschmidt | 8% |
| Cyclomethicone | 23% |
| Isododecane | 10% |
| $TiO_2$ | 7% |
| Composite pigment* | 0.5% |
| Pigment iron oxide | 2.5% |
| Nylon powder | 5% |
| Aqueous phase | |
| Demineralized water | 42% |
| Magnesium sulphate | 1% |
| Preserving agents | 1% |

*Mixture synthetic titanium dioxide**, D&C RED 7, polymethylhydrogensiloxane (respective weight proportions $TiO_2$: 65.8/D&C RED 7: 32.9/binder: 1.3)
**$TiO_2$ having BET specific surface of 50 $m^2$/g and a mean size of 20 nm.

Example 3

Lipstick

| | |
|---|---|
| Octyldodecanol | 15.61% |
| BHT | 0.06% |
| Isopropyl lanolate | 9.60% |
| Acetylated lanolin | 9.60% |
| Phenyl trimethicone | 4.26% |
| Diisostearyl malate | 13.07% |
| Lanolin oil | 9.60% |
| Tridecyl trimellitate | 10.40% |
| Polyethylene | 8.8% |
| Microcrystalline wax | 4% |
| Hydrogenated coco-glycerides | 5% |
| Composite pigment* | 10.00% |

*Mixture synthetic titanium dioxide**, D&C RED 7, polymethylhydrogensiloxane (respective weight proportions TiO$_2$: 65.8/D&C RED 7: 32.9/binder: 1.3)
**TiO$_2$ having BET specific surface of 50 m$^2$/g and a mean size of 20 nm.

Example 4

Lipstick

| | |
|---|---|
| Octyldodecanol | 14.42% |
| BHT | 0.06% |
| Isopropyl lanolate | 8.87% |
| Acetylated lanolin | 8.87% |
| Phenyl trimethicone | 3.94% |
| Diisostearyl malate | 12.07% |
| Lanolin oil | 8.87% |
| Tridecyl trimellitate | 9.60% |
| Polyethylene wax | 8.8% |
| Microcrystalline wax | 4% |
| Hydrogenated coco-glycerides | 5% |
| Composite pigments* | 15.0% |
| FD&C Blue 1 Al Lake | 0.5% |

*Mixture synthetic titanium dioxide**, D&C RED 7, polymethylhydrogensiloxane (respective weight proportions TiO$_2$: 65.8/D&C RED 7: 32.9/binder: 1.3)
**TiO$_2$ having BET specific surface of 50 m$^2$/g and a mean size of 20 nm.

For this composition, the following measurements can be made:

| | |
|---|---|
| $L^*_{bulk}$ | 29.7 |
| $a^*_{bulk}$ | 31.2 |
| $b^*_{bulk}$ | 7 |
| $L^*_{application}$ | 33.0 |
| $a^*_{application}$ | 41.7 |
| $b^*_{application}$ | 9.9 |
| $C^*_{application}$ | 42.9 |
| Covering power | 95.4 |
| $\Delta E$ | 10.9 |

Example 5

Lipstick

| | |
|---|---|
| Octyldodecanol | 13.45% |
| BHT | 0.05% |
| Isopropyl lanolate | 8.27% |
| Acetylated lanolin | 8.27% |
| Phenyl trimethicone | 3.67% |
| Diisostearyl malate | 11.26% |
| Lanolin oil | 8.27% |
| Tridecyl trimellitate | 8.96% |
| Polyethylene wax | 8.8% |
| Microcrystalline wax | 4% |
| Hydrogenated coco-glycerides | 5% |
| First composite pigment* | 15.0% |
| Second composite pigment*** | 5% |

*Mixture synthetic titanium dioxide**, FD&C Yellow 5 Al Lake, polymethylhydrogenesesiloxane (respective weight proportions TiO$_2$: 65.8/FD&C Yellow 5 Al Lake 32.9/binder 1.3).
**TiO$_2$ having BET specific surface of 50 m$^2$/g and a mean size of 20 nm.
*Mixture synthetic titanium dioxide, D&C Red 7, polymethylhydrogensiloxane (respective weight proportions: TiO$_2$: 65.8/D&C Red 7: 32.9/binder 1.3).

Example 6

Lipstick

| | |
|---|---|
| Octyldodecanol | 14.55% |
| BHT | 0.06% |
| Isopropyl lanolate | 8.93% |
| Acetylated lanolin | 8.93% |
| Phenyl trimethicone | 3.96% |
| Diisostearyl malate | 12.16% |
| Lanolin oil | 8.93% |
| Tridecyl trimellitate | 9.68% |
| Polyethylene | 8.8% |
| Microcrystalline wax | 4% |
| Hydrogenated coco-glycerides | 5% |
| Composite pigment* | 15% |

*Mixture synthetic titanium dioxide**, D&C RED 7, polymethylhydrogenosiloxane (respective weight proportions TiO$_2$: 65.8/D&C RED 7 32.9/binder 1.3).
**TiO$_2$ having BET specific surface of 50 m$^2$/g and a mean size of 20 nm.

For this composition, the following measurements can be made:

| | |
|---|---|
| $L^*_{bulk}$ | 33.9 |
| $a^*_{bulk}$ | 45.6 |
| $b^*_{bulk}$ | 15.3 |
| $L^*_{application}$ | 34.2 |
| $a^*_{application}$ | 52.5 |
| $b^*_{application}$ | 17.6 |
| $C^*_{application}$ | 55.4 |
| Covering power | 85 |
| $\Delta E$ | 7.2 |

Needless to say, the present disclosure is not limited to the working examples that have just been given.

It is possible to use composite pigments according to the present disclosure to prepare cosmetic compositions having formulations other than those given above.

The composite pigment may also be used to color a dermatological composition.

Throughout the description, including the claims, the term "comprising one" should be understood as being synonymous with "comprising at least one", unless the opposite is specified.

The ranges given should be understood as being inclusive of the limits, unless the opposite is specified.

The composition may be packaged in various manners, such as with or without an applicator.

The composition, when it is a stick, is for example packaged with a mechanism comprising a cup carrying the stick and drive means for driving the cup, these drive means comprising, for example, two pieces that can rotate one relative to the other and transform a rotation of the two pieces in an axial movement of the cup.

The composition may be packaged in a receptacle or other conditioning device that can be closed in a sealed manner, at least before the first use. This receptacle or other conditioning device may be made at least partially with thermoplastic materials or without any thermoplastic materials. The conditioning device may comprise a polyolefin.

When the composition is intended to be applied on the lips, and is in the form of a stick, the end of the stick may have a chamfered shape.

When the composition is intended to be applied with an applicator, the applicator may be chosen from a foam, an endpiece that may be flocked or not, a felt, a brush, and a comb.

An applicator may be housed releasably on the conditioning device containing the composition. In a variant, an applicator may be permanently fixed on the conditioning device containing the composition. The conditioning device containing the composition may be provided with a closure clasp or any other closure means, for example a magnetic closure or snaps.

A conditioning device containing the composition may be provided with a closure member that may be screwed, snapped or held by friction.

A conditioning device containing the composition may comprise sealing means, such as, for example, a sealing skirt or an elastomer seal. Such a seal may be overmolded or brought on the conditioning device.

A conditioning device containing the composition may comprise a label or a print, indicating for example a brand or a logo, and such a print can be made for example by hot transfer or cold transfer, or by serigraphy or other methods of printing.

The conditioning device containing the composition may comprise a cardboard packaging or a blister, for example at least partially made with a transparent plastic material.

What is claimed is:

1. A cosmetic composition comprising, in a physiologically acceptable medium, particles of at least one composite pigment comprising at least one binder and an inorganic core at least partially coated with at least one organic coloring substance, wherein the inorganic core comprises $TiO_2$, wherein the mean size of the inorganic core ranges from 1 nm to 100 nm, wherein the at least one organic coloring substance is present in an amount ranging from 10 to 500 parts by weight per 100 parts of the inorganic core, and wherein the color variation $\Delta E$ between the color of the bulk composition and the color after application is less than 20.

2. The composition according to claim 1, wherein the color variation $\Delta E$ is less than 15.

3. The composition according to claim 2, wherein the color variation $\Delta E$ is less than 10.

4. The composition according to claim 1, wherein the at least one binder comprises an organic binder.

5. The composition according to claim 1, wherein the at least one binder is chosen from silicone compounds, polymeric compounds, oligomeric compounds, and couplers.

6. The composition according to claim 5, wherein the at least one binder is chosen from organosilanes, fluoroalkyl organosilanes and polysiloxanes.

7. The composition according to claim 5, wherein the coupler is chosen from silanes, titanates, aluminates and zirconates.

8. The composition according to claim 5, wherein the at least one binder comprises a silicone polymer.

9. The composition according to claim 8, wherein the at least one binder comprises polymethylhydrogensiloxane.

10. The composition according to claim 1, wherein the composite pigment has less than 5% in weight of the binder relative to the total weight of the composite pigment.

11. The composition according to claim 1, wherein the composite pigment has less than 3% in weight of the binder relative to the total weight of the composite pigment.

12. The composition according to claim 1, wherein the composition is a composition to be applied to the lips.

13. The composition according to claim 12, wherein the composition is a lip gloss.

14. The composition according to claim 13, wherein the mean gloss $T_0h$ is higher than 30.

15. The composition according to claim 14, wherein the mean gloss $T_0h$ is higher than 50.

16. The composition according to claim 15, wherein the mean gloss $T_0h$ is higher than 70.

17. The composition according to claim 1, wherein the composition further comprises a fatty phase.

18. The composition according to claim 1, wherein the inorganic core further comprises at least one material chosen from metal salts, metal oxides other than $TiO_2$, aluminas, glasses, ceramics, graphite, silicas, silicates, aluminosilicates, borosilicates, and synthetic micas.

19. The composition according to claim 18, wherein the metal oxide other than $TiO_2$ is chosen from zirconium oxide, cerium oxide, zinc oxide, iron oxide, ferric blue and chromium oxide.

20. The composition according to claim 1, wherein the at least one composite pigment is present in the composition in an amount ranging from 0.1% to 20% by weight relative to the total composition weight.

21. The composition according to claim 20, wherein the at least one composite pigment is present in the composition in an amount ranging from 0.1% to 15% by weight relative to the total composition weight.

22. The composition according to claim 21, wherein the at least one composite pigment is present in the composition in an amount ranging from 0.5% to 10% by weight relative to the total composition weight.

23. The composition according to claim 1, wherein the composition does not comprise uncoated $TiO_2$ particles.

24. The composition according to claim 1, wherein the mean size of the inorganic core ranges from 10 nm to 50 nm.

25. The composition according to claim 1, wherein the saturation $C^*$ of the at least one composite pigment is greater than 30.

26. The composition according to claim 1, wherein the refractive index of the inorganic core is not less than 2.

27. The composition according to claim 1, wherein the at least one organic coloring substance does not comprise melanin.

28. The composition according to claim 1, wherein the at least one organic coloring substance comprises a lake.

29. The composition according to claim 1, wherein the density of the inorganic core is higher than the density of the at least one organic coloring substance.

30. The composition according to claim 1, wherein the density of the at least one composite pigment is higher than the density of the at least one organic coloring substance.

31. The composition according to claim 1, wherein the at least one organic coloring substance is fixed without any covalent bonds onto the inorganic core.

32. The composition according to claim 1, wherein the composite pigment does not comprise an interference pigment.

33. The composition according to claim 1, wherein the quantity Q of the particulate phase of the composition is more than 5% by weight relative to the total weight of the composition.

34. The composition according to claim 33, wherein the quantity of the particulate phase of the composition is more than 7.5% by weight relative to the total weight of the composition.

35. The composition according to claim 34, wherein the quantity of the particulate phase of the composition is more than 10% by weight relative to the total weight of the composition.

36. The composition according to claim 1, wherein $C^*_{application}$ is not less than 30.

37. The composition according to claim 36, wherein $C^*_{application}$ is not less than 40.

38. The composition according to claim 1, wherein the composition is a foundation.

39. The composition according to claim 1, wherein the composition is nail varnish.

40. The composition according to claim 1, wherein the composition is a mascara.

41. The composition according to claim 1, wherein the composition is a product for dying hair fibres.

42. A method for making up skin, lips, and integuments, comprising applying to the skin, lips, and integuments the composition of claim 1.

43. A method for making up skin, lips, and integuments, comprising applying to the skin, lips, and integuments a composition comprising, in a physiologically acceptable medium, at least one oil in an amount ranging from 0.1% to 90% by weight relative to the total weight of the composition and particles of at least one composite pigment comprising at least one binder and an inorganic core at least partially coated with at least one organic coloring substance, wherein the inorganic core comprises $TiO_2$, wherein the mean size of the inorganic core ranges from 1 nm to 100 nm, and further wherein the color variation $\Delta E$ between the color of the bulk composition and the color after application is less than 20.

* * * * *